(12) United States Patent
Enno

(10) Patent No.: US 7,923,217 B2
(45) Date of Patent: Apr. 12, 2011

(54) SPECIFICITY IN THE DETERMINATION OF ANTITHROMBIN

(75) Inventor: Adena Enno, Heidelberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 792 days.

(21) Appl. No.: 10/652,372

(22) Filed: Aug. 29, 2003

(65) Prior Publication Data

US 2004/0043428 A1 Mar. 4, 2004

(30) Foreign Application Priority Data

Aug. 29, 2002 (DE) .................................. 102 39 821

(51) Int. Cl.
*C12Q 1/46* (2006.01)
*G01N 33/557* (2006.01)
*C12N 15/15* (2006.01)

(52) U.S. Cl. ........................ 435/13; 436/517; 530/393

(58) Field of Classification Search ........................ None
See application file for complete search history.

(56) References Cited

U.S. PATENT DOCUMENTS

| | | | | |
|---|---|---|---|---|
| 4,219,497 A | * | 8/1980 | Plattner et al. | 548/542 |
| 4,314,987 A | * | 2/1982 | Morris et al. | 436/508 |
| 4,883,751 A | * | 11/1989 | Gitel et al. | 435/7.92 |
| 5,118,790 A | * | 6/1992 | Winant et al. | 530/324 |
| 5,308,755 A | * | 5/1994 | Nesheim et al. | 435/7.4 |
| 5,320,945 A | | 6/1994 | Dessauer et al. | |
| 5,693,641 A | | 12/1997 | Buckman et al. | |
| 5,721,214 A | | 2/1998 | Marlowe et al. | |
| 5,783,421 A | | 7/1998 | Zeelon et al. | |
| 5,891,647 A | | 4/1999 | Lormeau et al. | |
| 6,051,434 A | * | 4/2000 | Exner | 436/69 |
| 6,068,979 A | * | 5/2000 | Akhavan-Tafti | 435/6 |

FOREIGN PATENT DOCUMENTS

| | | |
|---|---|---|
| EP | 0 041 366 A1 * | 12/1991 |
| JP | 1017549 | 1/1989 |
| JP | 06094713 | 8/1994 |
| WO | EP 0 391 433 | 10/1990 |
| WO | EP 0 657 547 A1 | 6/1995 |
| WO | WO 96/40679 | 12/1996 |
| WO | WO 97/46523 | 12/1997 |
| WO | EP 0 927 767 A2 | 7/1999 |

OTHER PUBLICATIONS

Merriam-Webster's Online Dictionary, definition for the term "excess", retrieved from http://www.merriam-webster.com/dictionary/excess[1] on Oct. 18, 2008.*
Or Philo et al. "Comparison of antithrombin III assays using biological and chromogenic substrates" Br J Haematol. Jan. 1982;50(1):147-56.*
Topper, M., et al., *Enzyme-linked immunosorbent assay for thrombin-antithrombin III complexes in horses*; AJVR, 57(4):427-431 (1996).
Ruzzenente, O., et al., *Use of Purified Dermatan Sulfate for heparin Cofactor II (HC II) Assay*; Thrombosis Research; 65:281-287 (1992).
Pelzer, H., et al.. *Determination of Human thrombin-Antithrombin II Complex in Plasma with an Enzyme-Linked Inununosorbent Assay*; Thrombosis and Haemostasis, 59(1):101-106 (1988).
Demers, C., et al., *An Antithrombin III Assay Based on Factor Xa Inhibition Provides a More Reliable Test to Identify Congenital Antithrombin III Deficiency Than an Assay Based on Thrombin Inhibition*; Thrombosis and Haemostasis; 69(3):231-235 (1993).
Hickey, et al. *Clinical evaluation of a new FXa-based Antithrombin assay on Sysmex® CA-1500 System*, 2008 GTH Congress (Congress of Gesellschaft Für Thrombose-und-Hämostaseforschung, held Feb. 20-23, 2008, Wiesbaden, Germany.
H. Stormorken, *New Methods for the Analysis of Coagulation Using Chromogenic Substates; Studies on Antithrombin III Using Chromozyn TH*, Proceedings of the Symposium of the Deutsche Gessellschaft Fur Klinische Chemie, 119-121 (1976).
Odegard, et al. *Automated Antithombin III Assay with a Centrifugal Analyser*, Haemostasis, 7:202-209 (1978).
Fareed, et al. *Current status of methodologies for antithrombin III and heparin with the advent of peptide chromogenic substrates*, Chromogenic Peptide Substrates, 183-191 (1979).
Abildgaard, et al. *Antithrombin (Heparin Cofactor) Assay with "New" Chromogenic Substrates (S-2238-Chromozyn TH)*, Thrombosis Research, 11:549-553 (1977).
Ostrem, et al. *Discovery of a Novel, Potent, and Specific Family of Factor Xa Inhibitors via Combinatorial Chemistry*, Biochemistry, 37:1053-1059 (1998).
Lill, et al., Methods of Enzymatic Analysis, published in Bergmeyer, Methods in Enzymatic Analysis, 3rd Edition, Verlag Chemie, 5:441-448 (1986).
Witt, et al., Neu Methoden der Gerinnungsanalyse mit chromagenen Substraten, J. Clin. Chem. Clin. Biochem, 15:239-244 (1977) (concise explanation in specification, paragraph [0003]).

* cited by examiner

*Primary Examiner* — Gailene R Gabel
*Assistant Examiner* — Christine Foster
(74) *Attorney, Agent, or Firm* — McDonnell Boehnen Hulbert & Berghoff LLP

(57) ABSTRACT

Methods and reagents for determining antithrombin III (AT) in body fluids by adding an AT binding partner to the sample and determining the free AT binding partner.

10 Claims, No Drawings

SPECIFICITY IN THE DETERMINATION OF ANTITHROMBIN

BACKGROUND OF THE INVENTION

1. Field of the Invention

The invention concerns a method for determining antithrombin III (AT) in body fluids by adding an AT binding partner to the sample and determining the free AT binding partner. It also concerns a reagent that is suitable for this method.

2. Description of Related Art

AT is a factor of the blood coagulation system which plays a regulatory role. Blood coagulation is initiated by a cascade-like interaction of various proteases. The last of the successive activation steps releases thrombin, which in turn generates fibrin monomers which associate to form a thrombus. The most important regulator is AT, which can form a complex with thrombin and also with other proteases involved in blood coagulation that blocks the active center. The AT content in the blood of healthy humans is within a relatively narrow range. Reduced AT contents may be due to consumptive coagulopathy, a severe liver disease or they may be hereditary. A reduced AT content is nowadays generally regarded to be a risk for thrombosis. Hence in some cases the AT content is even reduced in an acute thrombosis. Therefore the AT content is a valuable parameter in clinical diagnostics.

Various methods are already known for detecting AT in which an AT binding partner is added to a sample under conditions that allow an interaction of the AT binding partner with AT present in the sample and subsequently determining the amount of free AT partner. Such determinations may, for example, be based on immunological methods or use chromogenic substrates. In the latter case, thrombin or activated factor X is, for example, added to the sample which interacts with the AT present in the sample. Excess thrombin is then determined by incubation with a chromogenic substrate which forms a coloured substance due to the action of thrombin and evaluation of the colour generation where the AT content is indirectly proportional to the colour formation. Methods for determining AT are described, for example, in Bergmeyer, Methods of Enzymatic Analysis, 3rd edition, "Verlag Chemie", vol. 5, p. 441-448; I. Witt, ed., "Neue Methoden der Gerinnungsanalyse mit chromogenen Substraten", Stormorken, "Neue Methoden der Gerinnungsanalyse", page 119-121; Odegard et al., Haemostasis 7: 202-209 (1978); Fareed et al., Chromogenic Peptide Substrates (eds. M. F. Scully and V. V. Kakkar) Churchill Livingstone (1979) 183-191 and Abildgaard et al., Thromb. Res. 11, 549-553 (1977).

A disadvantage of known methods for detecting AT by adding thrombin is that a false high AT value is obtained in the presence of interfering factors, e.g., drugs such as hirudin that can themselves interact with thrombin. This disadvantage can be avoided by using activated factor Xa instead of thrombin. However, at present several factor Xa inhibitors are under development as therapeutic agents (Ostrem et al., Biochemistry 37 (1998), 1053-1059; U.S. Pat. Nos. 5,783,421; 5,721, 214; WO 96/40679; U.S. Pat. No. 5,693,641; WO 97/46523; JP-96-191434 etc.). When these agents come onto the market, the same problems will occur with a factor Xa-based detection method as with the thrombin-based test.

Hence the object of the invention was to improve known detection methods and to provide a method that leads to a reliable measured result even in the presence of interfering factors in the sample to be tested.

SUMMARY OF THE INVENTION

This object is achieved by a method for detecting antithrombin III (AT) in a sample which may contain an interfering factor comprising:

(a) contacting the sample with a first reagent R1 containing an AT binding partner under conditions where the AT binding partner essentially does not interact with AT but interacts with the interfering factor, (b) adding a second reagent R2 for a first determination of the free fraction of the AT binding partner, (c) adding a third reagent R3 to change the conditions such that the AT binding partner interacts with AT and carrying out a second determination of the free fraction of AT binding partner, and (d) determining the AT content in the sample from the difference between the first and second determination of the free fraction of the AT binding partner.

DETAILED DESCRIPTION

The method according to the invention comprises the detection of AT in a sample, in particular in a body fluid such as blood or plasma, based on determining the interaction of an AT binding partner with AT present in the sample wherein a first determination of the AT binding partner is carried out without AT interaction, and subsequently a second determination of the AT binding partner is carried out with AT interaction, and the AT content of the sample is determined from the difference between the first and second determination.

The method according to the invention is based on determining the free fraction of AT binding partner in the sample under different conditions. A first determination of the AT binding partner is carried out without AT interaction, i.e., under conditions where AT that is present essentially does not react with the AT binding partner, i.e., there is no interaction or only to an extent that does not substantially impair the determination due to the fact that AT is, for example, not present in an active form. Subsequently the conditions are changed such that AT present in the sample can interact with the AT binding partner by, for example, adding a suitable reagent to set up conditions under which the interaction, e.g., complex formation between AT and AT binding partner, is accelerated. The subsequent second determination of the remaining free (and active) AT binding partner allows an inference about the AT content of the sample.

The free AT binding partner can basically be determined by any method. Chromogenic determinations of activity are preferred in which, for example, the proteolytic activity of AT binding partners such as thrombin or factor Xa is determined, or an immunological determination is carried out in which, for example, antibodies are used which are specifically directed towards an AT binding partner that is not complexed (with AT) and which do not interfere with the subsequent complex formation between AT and AT binding partners.

A particularly preferred embodiment of the method according to the invention consists of determining the proteolytic activity of an AT binding partner. In this method the proteolytic activity of the AT binding partner remaining after reaction with an interfering factor is determined under conditions where AT present in the sample cannot react or can only slightly react with the AT binding partner. Subsequently the formation of the complex between AT and AT binding partner is accelerated by, for example, activating the AT.

Complexes are formed in this process from activated AT and the binding partner. Such a complexed binding partner has essentially no more proteolytic activity. Subsequently the activity of the binding partner is again determined. The difference between the first and the second activity corresponds to the amount of AT in the sample.

The AT binding partner is a detectable substance and preferably a substance with protease activity that can form a complex with AT which preferably results in its inhibition. Examples of suitable AT binding partners are thrombin and factor Xa. Thrombin is particularly preferably used.

The AT binding partner is preferably detected by means of a chromogenic substrate which forms a colour due to the action of the AT binding partner and measurement of the resulting colour. Examples of preferred substrates are peptidic substrates, for example, the thrombin substrate Tos-Gly-Pro-Arg-p-nitroaniline (CHROMOZYM TH, Pentapharm AG, Switzerland) which is converted by thrombin to Tos-Gly-Pro-Arg-OH and p-nitroaniline. However, other substrates that are accepted by corresponding AT binding partners are of course also suitable.

In contrast to methods of the prior art, a first determination of the activity of the AT binding partner occurs in the method according to the invention under conditions where AT present in the sample cannot, or can only to a slight extent, complex the binding partner and inhibit its activity. Hence it is expedient to carry out the first determination in the absence of substances such as heparin which accelerate complex formation between AT and AT binding partner. Antagonists for the accelerator such as heparin antagonists, e.g., POLYBRENE (hexadimethrine bromide), can be optionally added in small amounts. The addition of heparin antagonists is especially expedient when a patient has been previously treated with heparin such that a (low) heparin concentration present in the sample leads to an undesired acceleration of the complex formation between AT and AT binding partner. The addition of antagonists can at least partially prevent this undesired acceleration.

After the first determination of the free AT binding partner, another reagent is preferably added to the reaction mixture which contains an accelerator of complex formation such as heparin. Subsequently a second activity is determined under conditions where AT present in the sample can complex the AT binding partner. The AT content in the sample can be determined from the difference between the first and the second determination. The measured signal is inversely proportional to the AT concentration in the sample. If required, the third reagent can also contain additional AT binding partners. In addition, additional substrate can be pipetted in another step if too much substrate has already been consumed in the first determination.

The AT binding partner is determined by methods that are basically known, for example, as described in the Antithrombin III test from Roche Diagnostics GmbH, Mannheim, Germany. The determination can, for example, comprise a kinetic test or a two-point determination.

The invention also concerns a reagent kit for the quantitative detection of AT in a sample comprising:
(a) a first reagent R1 containing an AT binding partner,
(b) a second reagent R2 to determine the free AT binding partner, and
(c) a third reagent R3 containing an accelerator for the interaction between AT and AT binding partner where the third reagent R3 is separate from the first reagent R1.

The first reagent R1 is free of an accelerator for the interaction, which is, for example, a complex formation between AT and AT binding partner. The first reagent can optionally also contain an antagonist for such an accelerator. The second reagent R2 for determining the AT binding partner can be a suitable reagent for a chromogenic determination which, for example, contains a substrate for the AT binding partner. Furthermore, the second reagent may also be suitable for an immunological determination and, for example, contain antibodies against a free, unbound AT binding partner and optionally other reagents for carrying out an immunological test, e.g., a latex test. The third reagent R3 is separate from the first reagent R1 and contains an accelerator for the interaction, such as a complex formation, between AT and AT binding partner and is preferably heparin.

The determination can be carried out on conventional automated analysers such as the ROCHE/Hitachi and COBAS INTEGRA clinical chemistry analyzers (Roche Diagnostics Corporation).

The method according to the invention is further illustrated by the following example.

EXAMPLE

Determination of Antithrombin III in the Presence of Lepirudin

3 µl sample solution was pipetted into a measuring cuvette. 175 µl reagent R1 was added by pipette. The reagent R1 consisted of 100 mM Tris-HCl, 270 mM NaCl, 12 mM EDTA, 10 g/l polyethylene glycol 6000, 1 g/l bovine serum albumin, 0.5 NIH/ml bovine thrombin and a suitable amount of a fibrin polymerization inhibitor such as GPAP, pH 8.10. It was subsequently incubated for 5 min., and then 75 µl reagent R2 (CHROMOZYM TH 1.9 mM) was added. Then the first thrombin activity was determined in a kinetic test by a continuous bichromatic measurement at 415 and 700 nm (primary and secondary wavelength).

Finally 175 µl reagent R3 (100 mM Tris-HCl, pH 8.1; heparin 2 USP-U/ml; bovine thrombin (3.5 NIH/ml; 140 mM NaCl) was added, and the second thrombin activity was determined in a kinetic test by continuous measurement. The AT content was determined from the difference between the second and first thrombin activity according to the instructions of the Antithrombin III kit of Roche Diagnostics GmbH, Mannheim.

This determination was carried out in the presence of different amounts of hirudin (lepirudin, REFLUDAN, Aventis) (0, 1, 2, 4 and 8 µg/ml).

The results are shown in the following table.

| lepirudin (µg/ml) | AT concentration (%) found (invention) | deviation (%) with the test according to the invention | deviation (%) with the test according to the prior art |
|---|---|---|---|
| 0 | 100 | — | — |
| 1 | 100 | 0 | 5 |
| 2 | 99.9 | 0 | 10 |
| 4 | 102.5 | 3 | 25 |
| 8 | 130.0 | 30 | 52 |

The table shows that the lepirudin interference can be completely (deviation <5%) eliminated up to a concentration of 4 µg/ml. The therapeutic concentrations when administering lepirudin are usually within this range, and hence the method according to the invention reliably determines the AT content even in the presence of drugs that may potentially interfere.

What is claimed is:

1. A method for determining the antithrombin III (AT) content in a sample that may contain one or more pharmaceutical compounds that inhibit thrombin, the method comprising:
   (a) providing a reaction mixture by contacting the sample with a first reagent R1 comprising thrombin, under conditions wherein the thrombin essentially does not interact with AT but interacts with the one or more pharmaceutical compounds that inhibit thrombin, if present,
   (b) adding to the reaction mixture a second reagent R2 comprising a chromogenic substrate which is a peptide substrate for thrombin, and determining the amount of thrombin activity in the reaction mixture,
   (c) changing the conditions of the reaction mixture by adding to the reaction mixture a third reagent R3 comprising heparin such that thrombin interacts with AT,
   (d) conducting a second determination of the thrombin activity in the reaction mixture, wherein the determination comprises using the reagent R2,
   (e) determining the difference between the first and second determinations of thrombin activity, and
   (f) determining the AT content of said sample from said difference determined in step (e).

2. The method of claim 1 wherein the first reagent R1 further comprises an antagonist for heparin.

3. The method of claim 2 wherein the first reagent R1 comprises hexadimethrine bromide.

4. The method of claim 1 wherein the third reagent R3 further comprises additional thrombin.

5. The method of claim 1 wherein said first and/or second determination of thrombin comprises a kinetic determination.

6. The method of claim 1, wherein the sample contains one or more pharmaceutical compounds that inhibit thrombin.

7. A method for determining the amount of antithrombin III (AT) in a sample containing one or more pharmaceutical compounds that inhibit thrombin, the method comprising:
   (a) providing a reaction mixture by mixing the sample with thrombin and an antagonist for heparin under conditions wherein the thrombin essentially does not interact with AT but interacts with the one or more pharmaceutical compounds that inhibit thrombin,
   (b) adding to the reaction mixture a chromogenic substrate which is a peptide substrate for thrombin, and conducing a first determination of the thrombin activity in the reaction mixture,
   (c) changing the conditions of the reaction mixture by adding heparin to the reaction mixture such that thrombin interacts with AT,
   (d) conducting a second determination of the thrombin activity in the reaction mixture using the chromogenic substrate,
   (e) determining the difference between the first and second determinations of thrombin, and
   (f) determining the AT content of said sample from said difference determined in step (e).

8. The method of claim 7 wherein the first reagent R1 comprises hexadimethrine bromide.

9. The method of claim 7 wherein the third reagent R3 further comprises additional thrombin.

10. The method of claim 7 wherein said first and/or second determination of thrombin comprises a kinetic determination.

* * * * *

UNITED STATES PATENT AND TRADEMARK OFFICE
CERTIFICATE OF CORRECTION

PATENT NO.      : 7,923,217 B2
APPLICATION NO. : 10/652372
DATED           : April 12, 2011
INVENTOR(S)     : Enno Adema It is certified that error appears in the above-identified patent and that said Letters Patent is hereby corrected as shown below:

Delete the Title page and insert the Title page attached.

Signed and Sealed this
Twenty-seventh Day of September, 2011

David J. Kappos
*Director of the United States Patent and Trademark Office*

(12) United States Patent
Adema

(10) Patent No.: US 7,923,217 B2
(45) Date of Patent: Apr. 12, 2011

(54) SPECIFICITY IN THE DETERMINATION OF ANTITHROMBIN

(75) Inventor: Enno Adema, Heidelberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 792 days.

(21) Appl. No.: 10/652,372

(22) Filed: Aug. 29, 2003

(65) Prior Publication Data

US 2004/0043428 A1 Mar. 4, 2004

(30) Foreign Application Priority Data

Aug. 29, 2002 (DE) .................................. 102 39 821

(51) Int. Cl.
*C12Q 1/46* (2006.01)
*G01N 33/557* (2006.01)
*C12N 15/15* (2006.01)

(52) U.S. Cl. ........................ 435/13; 436/517; 530/393

(58) Field of Classification Search .................... None
See application file for complete search history.

(56) References Cited

U.S. PATENT DOCUMENTS

| | | | | |
|---|---|---|---|---|
| 4,219,497 | A | * | 8/1980 | Plattner et al. ............... 548/542 |
| 4,314,987 | A | * | 2/1982 | Morris et al. ................. 436/508 |
| 4,883,751 | A | * | 11/1989 | Gitel et al. .................... 435/7.92 |
| 5,118,790 | A | * | 6/1992 | Winant et al. ................ 530/324 |
| 5,308,755 | A | * | 5/1994 | Nesheim et al. .............. 435/7.4 |
| 5,320,945 | A | | 6/1994 | Dessauer et al. |
| 5,693,641 | A | | 12/1997 | Buckman et al. |
| 5,721,214 | A | | 2/1998 | Marlowe et al. |
| 5,783,421 | A | | 7/1998 | Zeelon et al. |
| 5,891,647 | A | | 4/1999 | Lormeau et al. |
| 6,051,434 | A | * | 4/2000 | Exner ............................ 436/69 |
| 6,068,979 | A | * | 5/2000 | Akhavan-Tafti ............. 435/6 |

FOREIGN PATENT DOCUMENTS

| | | |
|---|---|---|
| EP | 0 041 366 A1 * | 12/1991 |
| JP | 1017549 | 1/1989 |
| JP | 06094713 | 8/1994 |
| WO | EP 0 391 433 | 10/1990 |
| WO | EP 0 657 547 A1 | 6/1995 |
| WO | WO 96/40679 | 12/1996 |
| WO | WO 97/46523 | 12/1997 |
| WO | EP 0 927 767 A2 | 7/1999 |

OTHER PUBLICATIONS

Merriam-Webster's Online Dictionary, definition for the term "excess", retrieved from http://www.merriam-webster.com/dictionary/excess[1] on Oct. 18, 2008.*
Or Philo et al. "Comparison of antithrombin III assays using biological and chromogenic substrates" Br J Haematol. Jan. 1982;50(1):147-56.*
Topper, M., et al., *Enzyme-linked immunosorbent assay for thrombin-antithrombin III complexes in horses*; AJVR, 57(4):427-431 (1996).
Ruzzenente, O., et al., *Use of Purified Dermatan Sulfate for heparin Cofactor II (HC II) Assay*, Thrombosis Research; 65:281-287 (1992).
Pelzer, H., et al., *Determination of Human thrombin-Antithrombin II Complex in Plasma with an Enzyme-Linked Immunosorbent Assay*; Thrombosis and Haemostasis, 59(1):101-106 (1988).
Demers, C., et al., *An Antithrombin III Assay Based on Factor Xa Inhibition Provides a More Reliable Test to Identify Congenital Antithrombin III Deficiency Than an Assay Based on Thrombin Inhibition*; Thrombosis and Haemostasis; 69(3):231-235 (1993).
Hickey, et al. *Clinical evaluation of a new FXa-based Antithrombin assay on Sysmex® CA-1500 System*, 2008 GTH Congress (Congress of Gesellschaft Für Thrombose-und-Hämostaseforschung, held Feb. 20-23, 2008, Wiesbaden, Germany.
H. Stormorken, *New Methods for the Analysis of Coagulation Using Chromogenic Substrates; Studies on Antithombin III Using Chromozyn TH*, Proceedings of the Symposium of the Deutsche Gessellschaft Fur Klinische Chemie, 119-121 (1976).
Odegard, et al. *Automated Antithombin III Assay with a Centrifugal Analyser*, Haemostasis, 7:202-209 (1978).
Fareed, et al. *Current status of methodologies for antithrombin III and heparin with the advent of peptide chromogenic substrates*, Chromogenic Peptide Substrates, 183-191 (1979).
Abildgaard, et al. *Antithrombin (Heparin Cofactor) Assay with "New" Chromogenic Substrates (S-2238-Chromozyn TH)*, Thrombosis Research, 11:549-553 (1977).
Ostrem, et al. *Discovery of a Novel, Potent, and Specific Family of Factor Xa Inhibitors via Combinatorial Chemistry*, Biochemistry, 37:1053-1059 (1998).
Lill, et al., Methods of Enzymatic Analysis, published in Bergmeyer, Methods in Enzymatic Analysis, 3rd Edition, Verlag Chemie, 5:441-448 (1986).
Witt, et al., Neu Methoden der Gerinnungsanalyse mit chromagenen Substraten, J. Clin. Chem. Clin. Biochem, 15:239-244 (1977) (concise explanation in specification, paragraph [0003]).

* cited by examiner

*Primary Examiner* — Gailene R Gabel
*Assistant Examiner* — Christine Foster
(74) *Attorney, Agent, or Firm* — McDonnell Boehnen Hulbert & Berghoff LLP

(57) ABSTRACT

Methods and reagents for determining antithrombin III (AT) in body fluids by adding an AT binding partner to the sample and determining the free AT binding partner.

10 Claims, No Drawings